(12) United States Patent
Pandya

(10) Patent No.: US 10,174,131 B2
(45) Date of Patent: Jan. 8, 2019

(54) BIOMASS PROCESSING METHOD

(71) Applicant: PLAXICA LIMITED, London, Greater London (GB)

(72) Inventor: Urvish Rameshchandra Pandya, Durham (GB)

(73) Assignee: Sappi Biotech UK Ltd, Redcar (GB)

( * ) Notice: Subject to any disclaimer, the term of this patent is extended or adjusted under 35 U.S.C. 154(b) by 0 days.

(21) Appl. No.: 15/302,376

(22) PCT Filed: Apr. 9, 2015

(86) PCT No.: PCT/GB2015/051081
§ 371 (c)(1),
(2) Date: Oct. 6, 2016

(87) PCT Pub. No.: WO2015/155534
PCT Pub. Date: Oct. 15, 2015

(65) Prior Publication Data
US 2017/0029532 A1 Feb. 2, 2017

(30) Foreign Application Priority Data
Apr. 9, 2014 (GB) .................................. 1406366.3

(51) Int. Cl.
*C07C 67/08* (2006.01)
*C08B 37/00* (2006.01)
(Continued)

(52) U.S. Cl.
CPC .......... *C08B 37/0057* (2013.01); *C07C 51/00* (2013.01); *C07C 67/08* (2013.01); *C13K 13/002* (2013.01)

(58) Field of Classification Search
CPC ...... C08B 37/0057; C07C 51/00; C07C 67/08
See application file for complete search history.

(56) References Cited

U.S. PATENT DOCUMENTS 2,037,001 A 4/1936 Aronovsky
2,166,540 A 7/1939 Bailey
(Continued)

FOREIGN PATENT DOCUMENTS

CN 101121735 A 2/2008
CN 102719283 A 10/2012
(Continued)

OTHER PUBLICATIONS

Wang, K., et al., "Organosolv fractionation process with various catalysts for improving bioconversion of triploid poplar," Jun. 9, 2012, pp. 1503-1509, vol. 47(10), Process Biochemistry.
(Continued)

*Primary Examiner* — Nicholas E Hill
(74) *Attorney, Agent, or Firm* — Dinsmore & Shohl LLP

(57) ABSTRACT

A process for the production of hemicellulose derived monosaccharides comprising: (a) contacting an aqueous hemicellulosic stream with a $C_{3-8}$ alkyl alcohol at elevated temperature and acidic pH to produce a reaction mixture comprising at $C_{3-8}$ alkyl ester and a hemicellulose-derived monosaccharide; and (b) separating the reaction mixture obtained from step (a) into an aqueous phase comprising said hemicellulose-derived monosaccharide and an organic phase comprising said $C_{3\text{-}O8}$ alkyl ester. The product of step (b) may be further processed using an optional step: (c) reacting said hemicellulose-derived monosaccharide obtained from step (b) with a metal hydroxide or a quaternary ammonium hydroxide to produce a metal lactate or quaternary ammonium lactate.

21 Claims, 3 Drawing Sheets

(51) Int. Cl.
C07C 51/00 (2006.01)
C13K 13/00 (2006.01)

(56) References Cited

U.S. PATENT DOCUMENTS

| | | | |
|---|---|---|---|
| 4,444,881 | A | 4/1984 | Urbas |
| 5,562,777 | A | 10/1996 | Farone et al. |
| 6,509,180 | B1 | 1/2003 | Verser |
| 2001/0014758 | A1 | 8/2001 | Baniel |
| 2010/0170504 | A1 | 7/2010 | Zhang |
| 2010/0190973 | A1 | 7/2010 | Srivastava |
| 2011/0015007 | A1 | 1/2011 | MacDougall |
| 2011/0165643 | A1 | 7/2011 | Retsina |
| 2011/0192560 | A1* | 8/2011 | Heikkila ............... C13B 20/148 162/29 |
| 2013/0178598 | A1 | 7/2013 | Kishida |
| 2013/0197183 | A1 | 8/2013 | Marshall |
| 2014/0048221 | A1 | 2/2014 | Li |
| 2014/9048222 | | 2/2014 | Li |
| 2014/0170713 | A1 | 6/2014 | Retsina |
| 2014/0227161 | A1* | 8/2014 | Manesh ............... C07C 45/00 423/437.1 |
| 2014/0227742 | A1 | 8/2014 | Bao |
| 2014/0273104 | A1 | 9/2014 | Paripati |
| 2014/0326421 | A1 | 11/2014 | Fallon |
| 2015/0141628 | A1 | 5/2015 | Jansen |

FOREIGN PATENT DOCUMENTS

| | | |
|---|---|---|
| FR | 2757539 | 6/1998 |
| GB | 400413 | 10/1933 |
| GB | 858286 | 1/1961 |
| WO | 2006124633 | 11/2006 |
| WO | 2012052703 | 4/2012 |
| WO | 2013138222 A1 | 9/2013 |

OTHER PUBLICATIONS

Huijgen, W.J.J., et al., "Fractionation of wheat straw by prehydrolysis, organosolv delignification and enzymatic hydrolysis for production of sugars and lignin," Mar. 7, 2012, pp. 389-398, vol. 114, Bioresource Technology.
Puls, J., et al., "Industrially Isolated Hemicelluloses," 2004, pp. 24-37, ACS Symposium Series; American Chemical Society.
McGee, J.K., et al., "Chemicals from renewable resources: Hemicellulose behavior during organosolv delignification of southern yellow pine," 1982, 49-56, vol. 19(1-3), Chemical Engineering Communications.
Huijgen, W.J.J., et al., "Modified organosols as a fractionation process of lignocellulosic biomass for co-production of fuels and chemicals," Jun. 2-6, 2008, 16th European Biomass Conference, Valencia, Spain, 5 pages.
Nie, X.N , et al., "Physicochemical and structural characterization of hemicelluloses isolated by different alcohols from rice straw," 2013, pp. 3817-3832, vol. 8(3), BioResources.
Sannigrahi, P., et al., "Fundamentals of biomass pretreatment by fractionation," 2013, pp. 201-222, Chap. 10 of Aqueous Pretreatment of Plant Biomass for Biological and Chemical Conversion to Fuels and Chemicals, First Edition, ed. Wyman, Wiley.
Christopher, L., "Adding value to Bioproducts from hemicellulose," 2012, 225-247, Chap. 14 of Global Perspectives on Sustainable Forest Management, ed. Okai.
Carvalheiro, F., et al., "Hemicellulose biorefineries: a review on biomass pretreatments," Nov. 2008, pp. 849-864, vol. 67, Journal of Scientific & Industrial Research.
Huijen W., et al., "Lignin production of organosolv fractionation of lignocellulosic biomass," 2010, International Biomass Valorisation Congress, Amsterdam, 22 pages.
Girio, F.M., et al., "Hemicelluloses for fuel ethanol: A review," 2010, pp. 4775-4800, vol. 101, Bioresource Technology.

Zhu, Z., et al., "One-pot hydrolysis of lignocelluloses mediated by black liquor," 2013, 229-234, vol. 128, Bioresource Technology.
Walton, S.L., et al., "Pre-extraction of hemicelluloses from hardwood chips using an alkaline wood pulping solution followed by kraft pulping of the extracted wood chips," 2010, pp. 12638-12645, vol. 49(24), Industrial & Engineering Chemistry Research.
Knill, C.J., et al., "Degradation of cellulose under alkaline conditions," 2003, pp. 281-300, vol. 51, Carbohydrate Polymers.
Husson, S.M., et al., "Carbon dioxide-sustained adsorption of lactic acid at pH>pKa of the acid," 1999, pp. 1625-1632, vol. 38, Industrial & Engineering Chemistry Research.
Mok, W.S.L., et al., "Uncatalyzed solvolysis of whole biomass hemicellulose by hot compressed liquid water," 1992, pp. 1157-1161, vol. 31, Industrial & Engineering Chemistry Research.
Walton, S.L., "Biological conversion of hemicellulose extract into value-added fuels and chemicals," 2009, Electronic Theses and Dissertations, Paper 226, 175 pages.
Boudrant, J., et al., "Mathematical modelling of cell suspension in high cell density conditions: Application to L-lactic acid fermentation using Lactobacillus casei in membrane bioreactor," Apr. 2005, pp. 1641-1647, vol. 40(5), Process Biochemistry (Abstract only).
Fan, Y., et al., "Binary organosolv system for direct conversion of cellulose to chemicals and fuel precursors," Mar. 16-20, 2014, 247th ACS National Meeting & Exposition, Dallas, American Chemical Society, 1 page (Abstract).
Wang, K., et al., "Comparative characterization of degraded lignin polymer from the organsolv fractionation process with various catalysts and alcohols," 2014, vol. 131(1), Journal of Applied Polymer Science, 1 page (Abstract).
Del Rio, L., et al., "The effect of varying organosolv pretreatment chemicals on the physicochemical properties and cellulolytic hydrolysis of mountain pine beetle-killed lodgepole pine," 2010, vol. 161(1-8), Applied Biochemistry and Biotechnology, 1 page (Abstract).
Vershal, V.V., "Investigation of kinetics of wood delignification in organic medium," Khimiya Rastitel 'nogo Syr'ya, 2000, 1 page (Abstract).
Jimenez, L., et al., "Use of butanol-water mixtures for making wheat straw pulp," 1999, vol. 33(2), Wood Science & Technology, 1 page (Abstract).
Nada, A., et al., "Kinetic study of delignification of bagasse with butanol-water organosolv pulping process," 1998, vol. 57(8), Journal of Scientific & Industrial Research, 1 page (Abstract).
Sun, R., et al., "Isolation and characterization of organosolv lignins from wheat straw," 1998, vol. 30(1), Wood and Science Fiber, 1 page (Abstract).
Hashem, K., et al., "Kinetic approach to interpret the delignification of Egyptian bagasse organosolv pulping process," 1997, vol. 56(3), Journal of Scientific & Industrial Research, 1 page (Abstract).
Nada, A., et al., "Bagasse pulping with butanol-water system," 1995, vol. 40(3), Research & Industry, 1 page (Abstract).
Nada, A., et al., "Spectroscopic studies of bagasse butanol lignin," 1995, vol. 46(3), Polymer Degradation & Stability, 1 page (Abstract).
Abramovitch, R.A., et al., "Organosolv pulping using a microwave oven," 1994, vol. 48(4), Holzforschung, 1 page (Abstract).
Balogh, D.T., et al., "Solvent effects on organosolv lignin from Pinus caribaea hondurensis," 1992, vol. 46(4), Holzforschung, 1 page (Abstract).
Terent'Eva, E.P., et al., "Changes in the structure of aspenwood during its organosolv pulping," 1990, vol. 3, Koksnes Kimija, 1 page (Abstract).
Rughani, J., et al., "Combined rapid-steam hydrolysis and organosolv pretreatment of mixed southern hardwoods," 1989, vol. 33(6), Biotechnology & Bioengineering, 1 page (Abstract).
Koell, P., et al., "Organosolv pulping of birch wood in a flow apparatus," 1987, vol. 41(2), Holzforschung, 1 page (Abstract).
April, G.C., et al., "Chemicals from wood by organic solvent delignification," 1983, vol. 85(13), Gov. Rep. Announce. Index (U.S.) 1985, 1 page (Abstract).
Holtzapple, M.T., et al., "The effect of organosolv pretreatment on the enzymic hydrolysis of poplar," 1984, vol. 26 (7), Biotechnology & Bioengineering, 1 page (Abstract).
Gast, D., et al., "Component separation of lignocelluloses by organosoiv treatment," 1983, Comm. Eur. Communities, 1 page (Abstract).

(56) References Cited

OTHER PUBLICATIONS

Hansen, S.M., et al., "Chemical feedstocks from wood: aqueous organic alcohol treatment," 1980, vol. 25(4), Preprints of Papers—ACS, Division of Fuel Chemistry, 1 page (Abstract).

April, G.C., et al., "Prehydrolysis achieves higher organosolv delignification," 1982, vol. 65(2), Tappi, 1 page (Abstract).

Hansen, S.M., "Predicting solvent effects in organosolv treatment of southern yellow pine," 1981, vol. 3(1), Biosources Digest, 1 page (Abstract).

Muurinen, E., "Organosolv pulping: A review and distillation study related to peroxyacid pulping,"—extracts from a thesis, (obtainable at http://herkules.oulu.fi/isbn9514256611/isbn9514256611.pdf, 2 pages (Abstract).

International Search Report and Written Opinion of the International Searching Authority for International Application No. PCT/GB2015/051081, dated Jul. 20, 2015, 8 pages.

\* cited by examiner

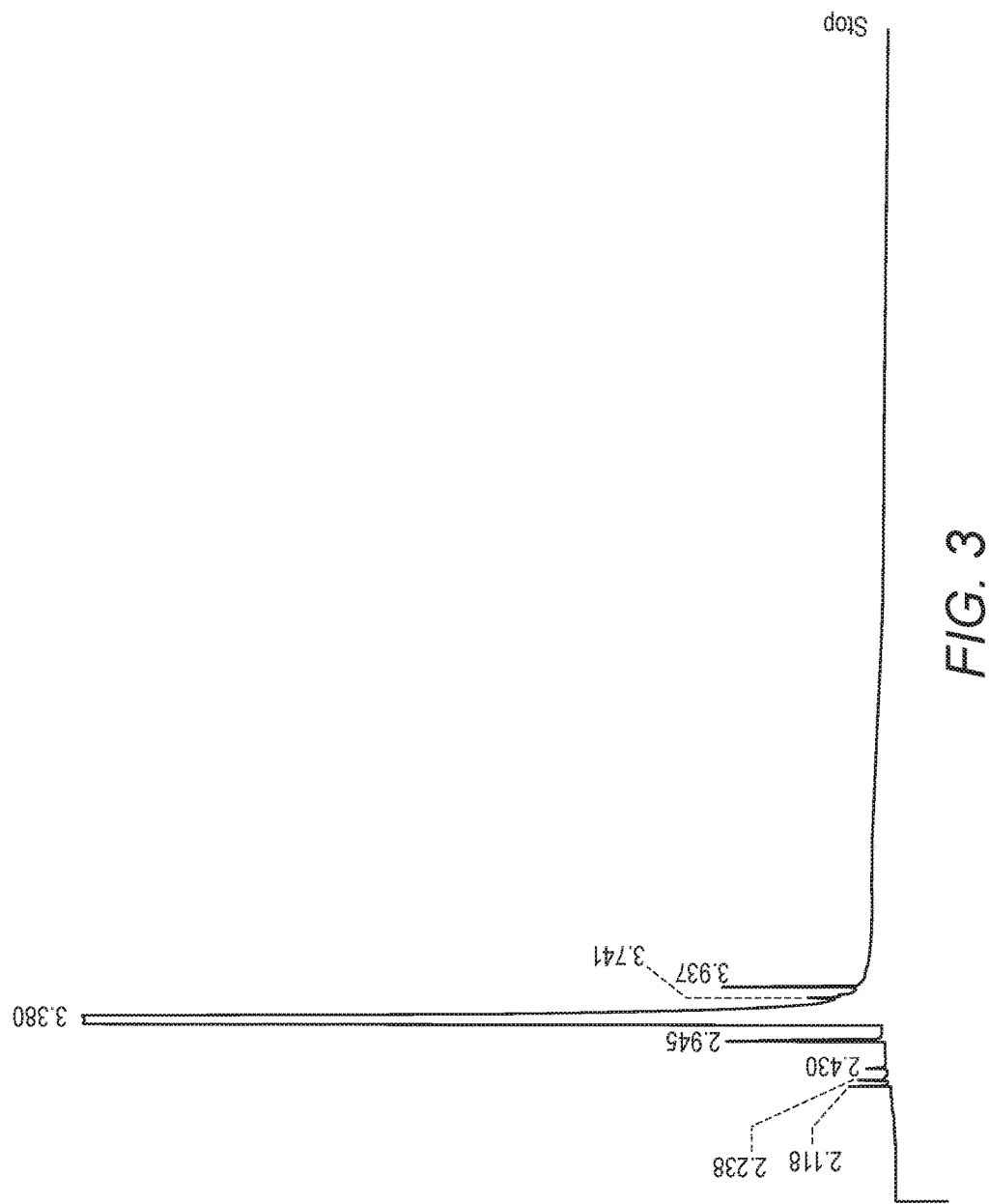

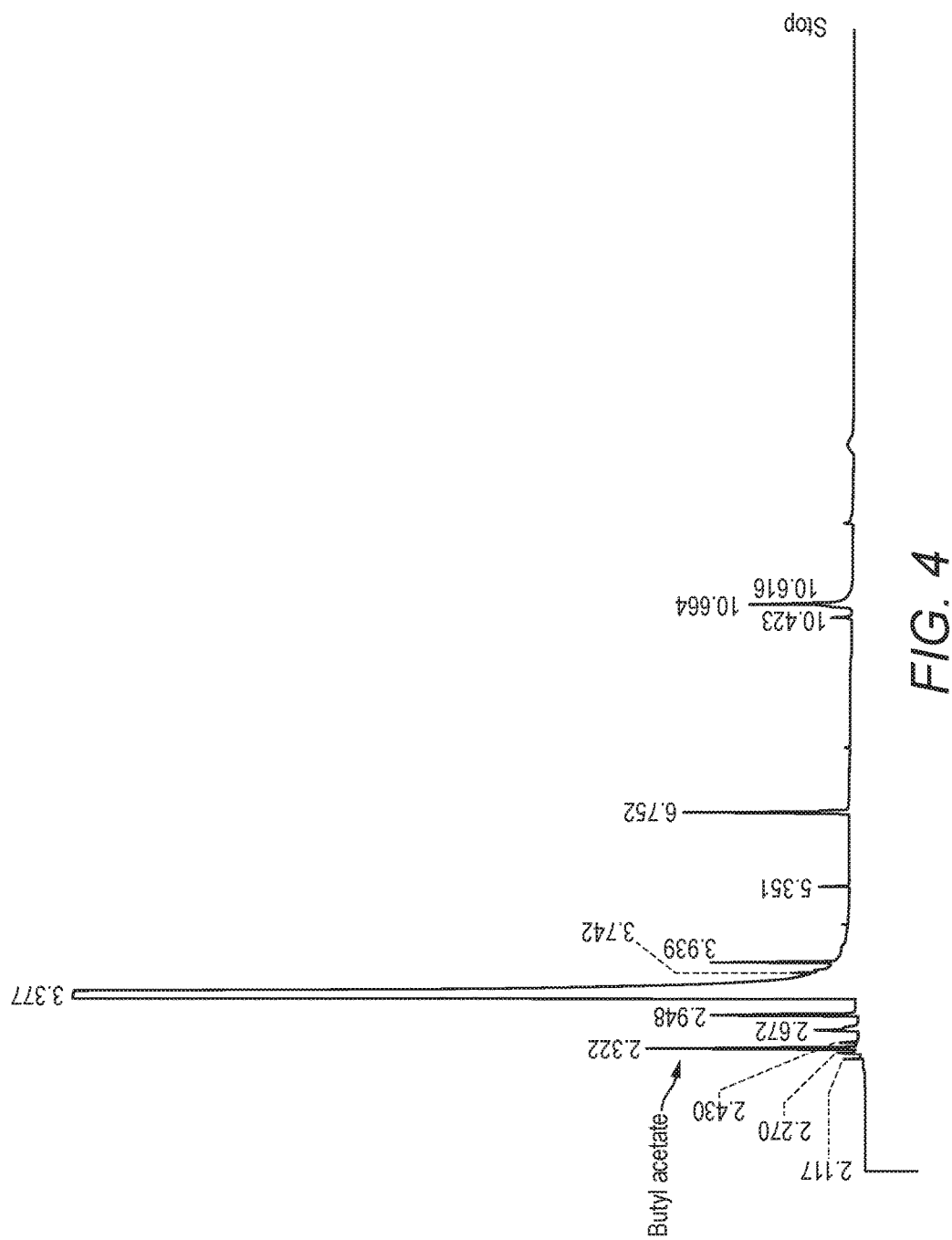

BIOMASS PROCESSING METHOD

CROSS REFERENCE TO RELATED APPLICATIONS

This application is a 371 application of International Application No. PCT/GB2015/051081, filed Apr. 9, 2015, which claims priority to GB Patent Application No. 1406366.3, filed Apr. 9, 2014, each of which is incorporated by reference in its entirety herein.

FIELD OF THE INVENTION

The present invention relates to processing of lignocellulosic biomass. In particular, it relates to a method of processing a hemicellulosic stream which has been obtained from biomass. The products obtained may be converted into chemical intermediates useful in the biopolymer industry. For example, the invention finds utility in processes for converting a hemicellulosic stream obtained from lignocellulosic biomass into a metal lactate or a quaternary ammonium lactate, as well as into downstream lactate-derived products such as lactic acid, lactide and polylactic acid.

BACKGROUND OF THE INVENTION

The three principal components of biomass are cellulose, lignin and hemicellulose, and they are present in almost all plant cell walls. The cellulosic material obtained from such biomass has a number of important industrial uses, notably in the production of paper from wood pulp. Accordingly a variety of processes have been developed for treating biomass to separate cellulosic material from other components of biomass, including the Kraft and sulfite processes. As well as producing cellulosic wood pulp, those processes also result in the production of by-products known as black liquor (Kraft process) or brown liquor (sulfite process) which typically contain hemicellulosic material together with lignin/lignin-derived products and inorganic chemicals. In recent times, demand for wood pulp containing higher cellulose content has been increasing, and processes for producing such forms of wood pulp (known as "dissolving pulp" or "dissolving cellulose") have been developed. Dissolving pulp finds use in the production of products such as rayon, viscose and cellophane. Typically in a process for producing dissolving pulp, an additional "pre-hydrolysis" stage is carried out in which lignocellulosic biomass is treated to remove hemicellulosic material and lignin/lignin-derived products, prior to subjecting the remainder of the cellulosic solids to further pulping conditions, such as Kraft conditions (treatment with an aqueous solution of sodium hydroxide and sodium sulphide at elevated temperature) or sulfite conditions (treatment with aqueous metal sulfite and/or bisulfite at elevated temperature). The separated hemicellulosic stream obtained from processes for producing dissolving pulp is typically referred to as "pre-hydrolysate liquor" or "pre-hydrolysis liquor", PHL.

Whilst the cellulosic material obtained from processes such as those outlined above is taken on and processed into various useful products, the hemicellulosic streams are often considered to be of little value and may be burnt or fed into a gasifier to recover their energy value.

A further, more recent, example of the use of cellulosic material as a feedstock in industrial processes is in the field of bioethanol production. Processes for the production of those biofuels from crop sources such as sugar beet and sweet sorghum have been developed and refined, and there has been a significant rate of growth in biofuel production in recent years. However, the identification of suitable feedstocks for the production of chemicals can be complicated. For instance, the increase in biofuel production has led to competition for crops, crop-switching and price increases for food products. Typically, the first stages of cellulosic ethanol production involve pre-treatment of biomass and removal of the hemicellulosic fraction, with the separated cellulosic material subsequently being converted into bioethanol by hydrolysis to glucose and subsequent fermentation to ethanol. The use of hemicellulosic material as a feedstock for bioethanol production has also been investigated. However, the effectiveness of fermentation of hemicellulosic feedstocks is limited by the fact that unlike cellulosic feedstocks they contain a mixture of pentose and hexose sugars which is typically harder for microorganisms to utilise. Additionally, hemicellulosic feedstocks tend to contain acids, aldehydes, furan derivatives and lignin-derived products which can act to inhibit the effectiveness of fermentation-utilising processes, due to the sensitivity of the species of microorganisms typically employed to those compounds. As a result, hemicelluloses currently represent the largest polysaccharide fraction wasted in most cellulosic ethanol pilot and demonstration plants around the world (Girio et al, Bioresource Technology, 2010, 101 p 4775-4800).

One well-known method of treating biomass is the "organosolv" process. This process involves treating whole biomass with one of a variety of organic solvents, for example an alcohol, and the result of the process is generally three product streams: cellulose, hemicellulose and lignin. Much research has been carried out to determine suitable conditions under which the organosolv process can be performed to optimise yields of the desired products. For example, Wang et al, Process Biochem. 47 (2012) 1503-1500, describes a series of experiments to determine the effects of varying catalysts and solvents in the organosolv process, producing "useful data for the application of mild organosolv fractionation on the utilization of whole biomass, especially for the recovery of hemicellulosic components."

Hiujgen et al, Bioresource Tech. 114 (2012) 389-398 describes a development of the organosolv process in which the biomass is pretreated in order to hydrolyse part of the biomass, specifically the hemicellulose, into sugars. These sugars are removed as part of a liquid stream, leaving a wet pulp stream which is relatively rich in cellulose and lignin (the hemicellulose having been degraded and removed), and which is subsequently treated using the organosolv process to remove the lignin from the cellulose.

Lactic acid (2-hydroxypropanoic acid) and its cyclic dimer lactide (3,6-dimethyl-1,4-dioxan-2,5-dione) are important building blocks for the chemical and pharmaceutical industries. One example of their use is in the manufacture of polylactic acid, the biodegradability of which makes it an attractive candidate to replace more conventional polymers. A number of processes are known for producing lactic acid, including chemical synthesis and fermentation methods. According to Boudrant et al, Process Biochem. 40 (2005) p. 1642, "In 1987, the world production of lactic acid averaged approximately equal proportions being produced by chemical synthesis and fermentation processes". Such chemical syntheses typically employed the hydrocyanation of acetaldehyde. However, chemical processes of this type have long been regarded as inefficient on an industrial scale, and today virtually all large scale production of the lactic acid available commercially is manufactured by fermentation processes, see for example Strategic Analysis of the Worldwide Market for Biorenewable Chemicals M2F2-39, Frost and Sullivan, 2009. In a typical fermentation process, glucose is fermented by microorganisms to produce either D- or L-lactic acid, predominantly L-lactic acid. Companies such as Cargill and Corbion (formerly Purac) operate large-scale fermentation processes for the production of optically active lactic acid, and the patent literature is replete with improvements in such processes.

WO2012/052703 discloses a process for producing a complex of lactic acid and either ammonia or an amine, comprising reaction of one or more saccharides with barium hydroxide to produce a first reaction mixture comprising barium lactate, and contacting at least part of the first reaction mixture with ammonia or an amine and with carbon dioxide, or with the carbonate and/or bicarbonate salt of ammonia or an amine, to produce a second reaction mixture comprising the complex and barium carbonate. WO2012/052703 recommends the use of cellulose or starch as feedstocks. In particular, it refers to the use of invert sugar, or of glucose obtained from enzymatic hydrolysis of starch contained in biomass feedstocks such as maize, rice or potatoes. There is no mention of the possible use of hemicellulose.

Constituents of hemicellulose typically have a significant degree of acylation. For example, xylan hemicellulose is often found in a highly acetylated form. Conditions used for separating hemicellulosic material from cellulosic material typically result in significant quantities of organic acids (e.g. acetic acid, formic acid) being formed in the hemicellulosic stream. Accordingly, such streams would not be expected to be good feedstocks for production of lactic acid, due to contamination of the lactic acid product with other organic acids which may be difficult to separate.

We have now found an improved method of optimising the yields of useful products obtained from processes for the treatment of biomass. Specifically, we have found a process which allows the biomass to be treated in a first, conventional, step, to produce a hemicellulosic stream, and the hemicellulosic stream to be treated in subsequent steps to produce useful products. This invention gives efficient lignin removal from lignin-containing hemicellulosic streams and leads to high yields of hemicellulose-derived monosaccharides, which in turn leads to the unexpected result that hemicellulosic streams can be used inter alia as viable feedstocks for the production of lactate-containing species, chemical intermediates useful in the biopolymer and other industries. In particular, process conditions have been identified which enable metal lactate or quaternary ammonium lactate to be obtained in surprisingly good purity and in viable yield for use on an industrial scale.

SUMMARY OF THE INVENTION

The present invention provides a method of processing an aqueous hemicellulosic stream comprising:

(a) contacting an aqueous hemicellulosic stream with a $C_{3-8}$ alkyl alcohol at elevated temperature and acidic pH to produce a reaction mixture comprising a $C_{3-8}$ alkyl ester and a hemicellulose-derived monosaccharide; and (b) separating the reaction mixture into an aqueous phase comprising said hemicellulose-derived monosaccharide and an organic phase comprising said $C_{3-8}$ alkyl ester.

In one preferred embodiment of the invention, the process comprises an additional step:

(c) reacting said hemicellulose-derived monosaccharide obtained in step (b) with a metal hydroxide or a quaternary ammonium hydroxide to produce a metal lactate or quaternary ammonium lactate.

BRIEF DESCRIPTION OF THE DRAWINGS

FIG. 3 shows a GC chromatogram of a commercial sample of n-butanol. No peak corresponding to n-butyl acetate is visible.

FIG. 4 shows a GC chromatogram of a separated organic phase obtained following treatment of xylan with aqueous sulfuric acid and n-butanol at reflux for 3 hours and separation of the aqueous and organic phases. The GC chromatogram shows the presence of n-butyl acetate at 2.322 minutes. Peaks corresponding to lignin residues are also visible in the GC chromatogram at 5.351, 6.752, 10.423 and 10.664 minutes.

DETAILED DESCRIPTION OF THE INVENTION

Figure 1:
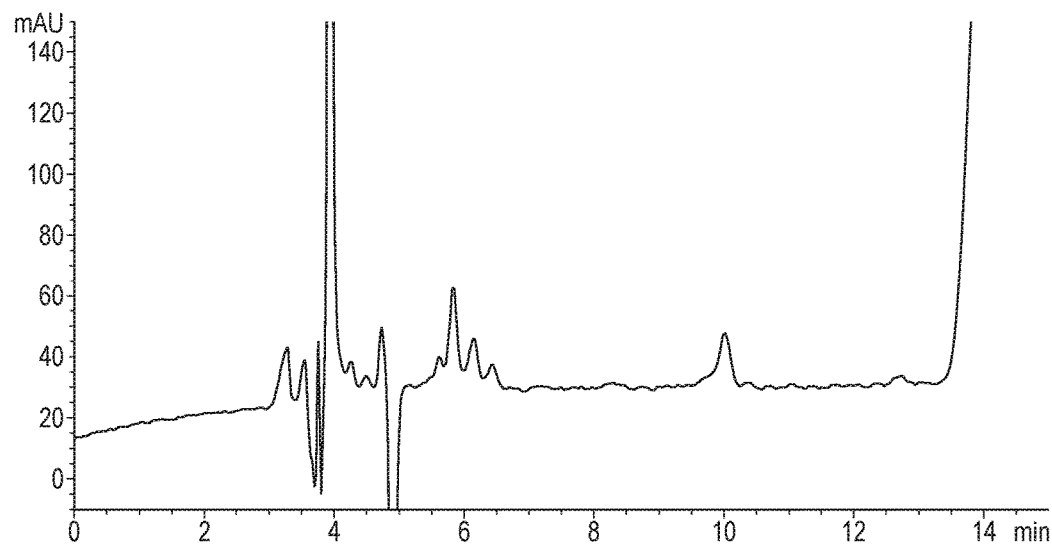
FIG. 1 shows an HPLC chromatogram of a separated aqueous layer following treatment of xylan with aqueous sulfuric acid and n-butanol at reflux for 3 hours, and separation of the aqueous and organic layers. No peak corresponding to acetic acid is visible.

As discussed above, hemicellulose is one of the three principal components of biomass, together with cellulose and lignin. Hemicelluloses are the second most abundant biopolymer in the plant kingdom after cellulose and they constitute, in general, 15-35% of plant biomass. Whereas cellulose is a highly uniform linear polysaccharide (it is a 1→4-β-linked polyglucan), the term hemicellulose defines a group of heterogeneous polysaccharides of comparatively low molecular weight, having a degree of polymerisation of from about 40 to about 600 (in many cases the degree of polymerisation is from about 80 to about 200). Most hemicelluloses are branched structures (see for example Ren and Sun, *Cereal Straw as a Resource for Sustainable Biomaterials and Biofuels; Chemistry, Extractives, Lignins, Hemicelluloses and Cellulose*, 2010, Chapter 4; also Girio et al, Bioresource Technology, 2010, 101 p 4775-4800).

Hemicelluloses have been classified into four groups: i) xyloglycans (xylans); ii) mannoglycans (mannans); iii) xyloglucans (XG); and iv) mixed-linkage β-glucans (Ren and Sun, *Cereal Straw as a Resource for Sustainable Biomaterials and Biofuels; Chemistry, Extractives, Lignins, Hemicelluloses and Cellulose*, 2010, Chapter 4).

Xylans comprise a β(1→4)-D-xylanopyranose backbone, and typically contain carbohydrate groups on the 2- or 3-position of backbone residues. Examples include glucuronoxylans (GX), arabino(glucurono)xylans (AGX), glucurono(arabino)xylans (GAX) and arabinoxylans (AX). Xylans are the most common hemicelluloses, and in particular are abundant in hardwood or annual plants.

Mannans have been categorised in two groups: i) galactomannans, which comprise a β(1→4) linked D-mannopyranose backbone; and ii) glucomannans, which have a backbone comprising D-mannopyranose and D-glucopyranose residues with β(1→4) linkages. Mannans may have varying degrees of branching, with D-galactopyranose groups on the 6-position of the mannose backbone.

Xyloglucans (XG) comprise a β(1→4)-linked D-glucopyranose backbone with D-xylanopyranose residues at the 6-position of glucopyranose residues. There are two categories of xyloglucans, depending on the nature of the xylanopyranose-containing side-chains. Xyloglucans comprising two xylanopyranose units followed by two glucanopyranose units are referred to as XXGG, and xyloglucans comprising three xylanopyranose units followed by one glucopyranose unit are referred to as XXXG. Additional side-chains may also be present.

Mixed linkage β-glucans have a D-glucopyranose backbone with mixed β linkages (1→3, 1→4).

Step (a) involves contacting an aqueous hemicellulosic stream with a $C_{3-8}$ alkyl alcohol at elevated temperature. In many industrial processes, following treatment of lignocellulosic biomass, a hemicellulosic stream and cellulosic solids are obtained and are separated from one another. The hemicellulosic stream contains a greater proportion by weight of hemicellulosic material relative to cellulosic material than the proportion by weight of hemicellulosic material relative to cellulosic material present in the lignocellulosic biomass itself. In other words, the hemicellulosic stream contains a fraction of lignocellulosic biomass-derived material that is enriched in hemicellulosic material over that present in the lignocellulosic biomass itself. Similarly, the cellulosic solids contain a greater proportion by weight of cellulosic material (i.e. cellulose and/or cellulose-derived saccharides) relative to hemicellulosic material than the proportion by weight of cellulosic material relative to hemicellulosic material present in the lignocellulosic biomass itself. As discussed above, processing of hemicellulosic streams into useful chemical products is more difficult than for cellulosic solids; however the present invention finds a use for such hemicellulosic streams and an effective method of processing such streams.

In one embodiment at least 60 wt %, or at least 70 wt %, or at least 80 wt %, or at least 90 wt %, or at least 95 wt % of the saccharide material present in the aqueous hemicellulosic stream is hemicellulosic material. In one embodiment less than 20 wt %, or less than 15 wt %, or less than 10 wt %, or less than 5 wt % of the saccharide material present in the aqueous hemicellulosic stream is cellulosic material. In one embodiment the aqueous hemicellulosic stream is free or substantially free of cellulosic material. In one embodiment at least 60 wt % of the lignocellulosic biomass-derived material present in the hemicellulosic stream is hemicellulosic material and less than 20 wt % of the lignocellulosic biomass-derived material present in the hemicellulosic stream is cellulosic material. In one embodiment at least 70 wt % of the lignocellulosic biomass-derived material present in the hemicellulosic stream is hemicellulosic material and less than 15 wt % of the lignocellulosic biomass-derived material present in the hemicellulosic stream is cellulosic material. In one embodiment at least 80 wt % of the lignocellulosic biomass-derived material present in the hemicellulosic stream is hemicellulosic material and less than 10 wt % of the lignocellulosic biomass-derived material present in the hemicellulosic stream is cellulosic material. The analysis of saccharide material may routinely be performed by chromatographic methods (principally HPLC), as described in standard procedures issued by organisations such as ASTM [D5896-96 (2012)], the National Renewable Energy Laboratory (TP-510-42623) and TAPPI (T-249).

The aqueous hemicellulosic stream may contain other components, for example it may include other components of biomass such as lignin or lignin-derived products. The method of the invention is particularly useful for the processing of lignin-containing hemicellulosic streams, and in a preferred embodiment, the hemicellulosic stream is one which contains lignin. Such streams are generally obtained by the processing of biomass by processes other than the organosolv process, for example by dissolving pulp processes such as those that may be operated at a Kraft pulp mill, or the sulfite process. Generally lignin-containing hemicellulosic streams obtained by such processes are regarded as a waste or low value stream. Accordingly, the invention is particularly valuable when carried out using a hemicellulosic stream which has been obtained by treatment of biomass by a method other than the organosolv process, i.e. by a method other than the fractionation of biomass into three separate streams, being a cellulosic stream, a hemicellulosic stream, and a lignin stream, using an organic solvent, particularly an alcohol, for example a $C_{2-8}$, especially $C_{3-8}$, alkyl alcohol. For example, the hemicellulosic stream may have been obtained by using one of the processes described in more detail below. It may for example have been obtained by the hydrolysis of wood chips using hot water under pressure, or using steam. Preferably the hemicellulosic stream has been obtained from a dissolving pulp process; such streams are referred to as "pre-hydrolysate liquors", or PHL.

Where the hemicellulosic stream contains lignin, the organic phase produced in step (b) will contain lignin in addition to the $C_{3-8}$ alkyl ester. Surprisingly, it appears to be the case that the presence of acid, for example added sulfuric acid, which is capable of catalysing both the esterification of organic acids present in the hemicellulosic stream and also the hydrolysis of any hemicellulose and/or hemicellulose-derived oligosaccharides present in the hemicellulosic stream, also enhances the extraction of lignin into the organic phase. This effect could not have been predicted, and the process of the invention provides a surprisingly efficient way of removing not only organic acid impurities from the hemicellulosic stream ("wood acids") but also lignin from the hemicellulosic stream.

Spent chemicals from initial processing of biomass may also be present in the hemicellulosic stream (e.g. metal sulfate and/or carbonate, or metal sulfites). The concentration of hemicellulosic material present in the aqueous hemicellulosic stream will be a characteristic of the biomass source and will depend on the conditions used to obtain the aqueous hemicellulosic stream from biomass. In one embodiment at least 1 wt %, at least 5 wt %, at least 10 wt %, at least 20 wt %, at least 30 wt %, at least 40 wt % or at least 50 wt % of the aqueous hemicellulosic stream is hemicellulosic material.

The hemicellulosic material in the hemicellulosic stream comprises hemicellulose, hemicellulose-derived oligosaccharides and/or hemicellulose-derived monosaccharides. Hemicellulose-derived oligosaccharides and monosaccharides may be obtained by hydrolysis of hemicellulose present in biomass. The proportions of the hemicellulose, hemicellulose-derived oligosaccharides and/or hemicellulose-derived monosaccharides present in the hemicellulosic stream will depend on the conditions used to obtain the hemicellulosic stream from lignocellulosic biomass.

The aqueous hemicellulosic stream may be obtained from lignocellulosic biomass by known methods. For example, selective separation of hemicellulosic material from lignocellulosic biomass may be achieved using alkaline agents (such as sodium, potassium, calcium or ammonium hydroxide). The hemicellulosic stream may also be obtained by ammonia fibre explosion (AFEX). In that process, lignocellulosic biomass is treated with liquid ammonia at a temperature in the range of from 40 to 140° C. under pressure (250 to 300 psi), the complex formed by lignin with hemicellulose and cellulose is broken down and some hydrolysis of hemicellulose takes place. In another example, a hydrothermal process such as autohydrolysis (use of compressed liquid hot water, e.g. at a temperature in the range of from 200 to 250° C.) or steam injection/steam explosion (e.g. treatment with steam at a temperature in the range of from 200 to 250° C.) may be used.

In one preferred embodiment, the aqueous hemicellulosic stream used in the process of the invention is obtained from a process for producing dissolving pulp. As discussed above, such processes typically involve an additional "pre-hydrolysis" stage in which lignocellulosic biomass is treated to remove hemicellulosic material and lignin/lignin-derived products, prior to subjecting the remainder of the cellulosic solids to further pulping conditions, such as Kraft conditions (treatment with an aqueous solution of sodium hydroxide and sodium sulphide at elevated temperature) or sulfite conditions (treatment with aqueous metal sulfite and/or bisulfite at elevated temperature). Preferred pre-hydrolysis conditions comprise contacting lignocellulosic biomass such as wood chips with an acid (e.g. a mineral acid) in the presence of water at elevated temperature. For example, in one particularly preferred embodiment lignocellulosic biomass is treated with dilute sulfuric acid (e.g. 0.2-5% v/v aqueous sulfuric acid, or at a sulfuric acid concentration in water of from 0.05M to 1.5M) at a temperature in the range of from 100 to 250° C., more preferably in the range of from 150 to 250° C. In another embodiment lignocellulosic biomass is treated with concentrated sulfuric acid (e.g. 10-30% v/v aqueous sulfuric acid, or at a sulfuric acid concentration in water of from 2.0M to 6.0M) at a temperature in the range of from 40 to 100° C.

Pre-hydrolysate liquor typically contains high quantities of hemicellulosic material as well as lignin and is particularly suitable for use in the process of the invention.

In one embodiment, the aqueous hemicellulosic stream used in the process of the invention is black liquor. As discussed above, black liquor is a by-product of the Kraft process and is an aqueous mixture containing hemicellulosic material together with lignin/lignin-derived products and inorganic chemicals (e.g. sodium sulphate, sodium carbonate). Typically, the black liquor obtained following digestion of biomass (e.g. wood chips) contains approximately 15% by weight solid material, and is termed weak black liquor. Subsequent processing of the weak black liquor, for example by evaporating water, results in a substance which typically contains up to about 65 to 80% by weight solid material, which is termed heavy black liquor.

In one embodiment, the aqueous hemicellulosic stream used in the process of the invention is brown liquor. As discussed above, brown liquor is a by-product of the sulfite process for making wood pulp, and is an aqueous mixture containing hemicellulosic material, lignin/lignin-derived products and inorganic chemicals. Brown liquor is also referred to as red liquor, thick liquor, spent liquor and sulfite liquor.

In one embodiment, the aqueous hemicellulosic stream used in the process of the invention is a hemicellulosic waste stream from a process for producing bioethanol (e.g. a process for producing bioethanol involving fermentation of cellulose hydrolysate).

In one embodiment, the aqueous hemicellulosic stream is a hemicellulosic stream from a process for producing sugars from biomass.

The proportions of hemicellulose, cellulose and lignin present in lignocellulosic biomass vary depending on the type of biomass, as do the proportions of different polysaccharides which make up the hemicellulose proportion of the biomass. In one preferred embodiment the biomass from which the hemicellulosic stream is obtained comprises a hardwood, for example an *Acer* (maple), *Populus* (aspen), *Betula* (birch), *Fagus* (beech), *Eucalyptus, Quercus* (oak) *Populus* (poplar) or *Liquidambar* (sweetgum). In one preferred embodiment the biomass from which the hemicellulosic stream is obtained comprises a softwood, for example an *Abies* (fir), *Larix* (larch), *Picea* (spruce) or *Pinus* (pine). In one preferred embodiment the biomass from which the hemicellulosic stream is obtained comprises a grass, for example a *Panicum* (e.g. *Panicum virgatum*, switch grass), a *Sorghum* (e.g. sweet sorghum) or a *Saccharum* (e.g. sugar cane).

If desired, the hemicellulosic stream may be pretreated before carrying out step (a). In one embodiment no pretreatment is carried out. In another embodiment, the hemicellulosic stream is concentrated to increase its solids content.

As mentioned above, one known method of treating lignocellulosic biomass involves the treatment of said biomass with an alcohol, and this process gives rise to a hemicellulosic stream. Hemicellulosic streams produced in this way may be used in the process of the invention, but preferably the hemicellulosic stream used in the present invention has not been obtained in this way.

The process of the invention may be carried out batch wise, or as a continuous or semi-continuous process. For example, the hemicellulosic stream may be processed as a succession of batches. Similarly, if desired, the hemicellulosic stream may be provided as a succession of batches (e.g. in a series of containers shipped from the location where the hemicellulosic stream is obtained from lignocellulosic biomass to the location where the process of the invention is carried out).

As discussed above, constituents of hemicellulose typically have a significant degree of acylation, and as hemicellulosic material is broken down, significant quantities of organic acids (e.g. acetic acid, formic acid) may be formed. Under the process conditions of the present invention, a significant proportion of the organic acids and/or acyl moieties forming part of the hemicellulosic material in the hemicellulosic stream are converted to the corresponding $C_{3-8}$ alkyl ester, permitting separation of the alkyl ester and hemicellulose-derived saccharide in organic and aqueous phases respectively and, following conversion of monosaccharide to lactic acid, resulting in a lactate product having improved purity.

In one preferred embodiment the alkyl alcohol is a $C_{3-6}$ alkyl alcohol. In one preferred embodiment the $C_{3-8}$ alkyl alcohol contains only one hydroxyl group. Examples of preferred alkyl alcohols include i-propanol, n-butanol, n-pentanol, n-hexanol and 2-ethylhexanol.

In one preferred embodiment, the alkyl alcohol is a $C_{4-8}$ alkyl alcohol containing only one hydroxy group. The use of a $C_{4-8}$ alkyl alcohol containing only one hydroxy group results in the presence of a biphasic mixture in step (b), facilitating removal of acyl-containing species in step (b) resulting in an improved purity feedstock for optional step (c), due to preferential partitioning of the alkyl esters, plus any lignin present, into the organic phase. Most preferably the $C_{3-8}$ alkyl alcohol is n-butanol.

Step (a) is carried out at acidic pH, i.e. at a pH of less than 7. Preferably step (a) is carried out at a pH of less than 5, less than 4, less than 3 or less than 2. If the aqueous hemicellulosic stream is itself acidic, simply contacting the hemicellulosic stream with $C_{3-8}$ alkyl alcohol at elevated temperature may be sufficient to produce $C_{3-8}$ alkyl esters. However, in some cases it may be preferred to add an acid in step (a) to catalyse the formation of the $C_{3-8}$ alkyl esters. Where an acid is added in step (a), it may for example be a mineral acid, or an organic acid such as trifluoroacetic acid or methanesulfonic acid. Alternatively a solid-state resin can be added as an acid catalyst. Preferably the acid added in step (a) is a mineral acid, more preferably a mineral acid selected from the group consisting of hydrochloric acid and sulfuric acid (e.g. concentrated hydrochloric acid or concentrated sulfuric acid). In one embodiment the acid is hydrochloric acid. In another embodiment the acid is sulfuric acid. In one embodiment concentrated sulfuric acid or concentrated hydrochloric acid is added, in a volume ratio in the range of from 0.1:100 to 3:100 relative to the total volume of solvent used in step (a).

Preferably step (a) is carried out at a temperature in the range of from 30 to 250° C.; more preferably in the range of from 70 to 200° C.; still more preferably in the range of from 90 to 170° C. or from 130 to 190° C. Where the $C_{3-8}$ alkyl alcohol used in step (a) is n-butanol, step (a) is for example carried out at a temperature in the range of from 95 to 150° C., or from 130 to 190° C.; or for example in the range of from 100 to 120° C. The use of higher temperatures can reduce the reaction time leading to improved process economics. Heating under reflux may be preferred in many cases.

Where step (a) is carried out batchwise, it may for example be carried out over a time period in the range of from 30 minutes to 48 hours; for example in the range of from 1 to 24 hours; for example in the range of from 1 to 12 hours, for example in the range of from 2 to 6 hours. In one preferred embodiment step (a) is carried out at a temperature in the range of from 70 to 200° C., and over a time period in the range of from up to 12 hours, for example from 1 to 12 hours. In another preferred embodiment step (a) is carried out at a temperature in the range of from 95 to 150° C., and over a time period in the range of from 2 to 6 hours. However, in a further preferred embodiment, higher temperatures and lower reaction times may be used, for example step (a) may be carried out at a temperature in the range of 130 to 190° C. for a time period of less than an hour, for example from 10 to 30 minutes.

As discussed above, a hemicellulosic stream is a stream comprising hemicellulose, hemicellulose-derived oligosaccharides and/or hemicellulose-derived monosaccharides, and the proportions of those constituents will vary depending on the process by which the hemicellulosic stream has been obtained. Where the hemicellulosic stream contains hemicellulose and/or hemicellulose-derived oligosaccharides, subjecting the hemicellulosic stream to the conditions of step (a) results in hydrolysis of the hemicellulose and/or hemicellulose-derived oligosaccharides, such that the proportion of hemicellulosic material in the product of step (a) that is hemicellulose-derived monosaccharide is greater than the proportion of hemicellulosic material in the hemicellulosic stream starting material that is hemicellulose-derived monosaccharide. In one preferred embodiment, the hemicellulosic stream is subjected to the conditions of step (a) until at least 80 wt %, at least 90 wt %, at least 95 wt %, or all or substantially all of the hemicellulose-derived saccharides present in the reaction mixture are hemicellulose-derived monosaccharides.

Where an acid is added in step (a), the hemicellulosic stream may be admixed with acid prior to, at the same time as, or after admixing with $C_{3-8}$ alkyl alcohol. For example, $C_{3-8}$ alkyl alcohol may be added to the hemicellulosic stream followed by the acid, and the mixture then heated at elevated temperature. Alternatively the acid may be added to the hemicellulosic stream and the mixture heated at elevated temperature, with the $C_{3-8}$ alkyl alcohol then being added and the resulting mixture being heated at elevated temperature for a further period. Alternatively the acid may be added to the $C_{3-8}$ alkyl alcohol, and the resulting mixture then added to the hemicellulosic stream and the mixture heated at elevated temperature.

Step (a) is typically carried out at ambient pressure, but it may be carried out at higher or lower pressure if desired.

In one preferred embodiment of step (a), the aqueous hemicellulosic stream is a pre-hydrolysate liquor obtained from a process for producing dissolving pulp, and the aqueous hemicellulosic stream is admixed with an acid selected from the group consisting of hydrochloric acid and sulfuric acid, and with n-butanol, at a temperature in the range of from 95 to 150° C., or from 130 to 190° C. In one preferred embodiment of step (a), the aqueous hemicellulosic stream is a pre-hydrolysate liquor obtained from a process for producing dissolving pulp, and the aqueous hemicellulosic stream is admixed with an acid selected from the group consisting of hydrochloric acid and sulfuric acid, and with n-butanol, at a temperature in the range of from 95 to 150° C., at ambient pressure, and over a time period in the range of from 2 to 6 hours; or at a temperature in the range of 130 to 190° C. for a time period of less than one hour, for example from 10 to 30 minutes.

In alternative embodiments of step (a), the aqueous hemicellulosic stream is a pre-hydrolysate liquor obtained from a process for producing dissolving pulp, and the aqueous hemicellulosic stream is admixed with an acid selected from the group consisting of hydrochloric acid and sulfuric acid and heated under reflux for an initial period; following optional cooling, the resulting reaction mixture is mixed with n-butanol and heated under reflux for a further period.

The conditions under which step (a) is carried out will determine whether the reaction mixture is a one-phase or a two-phase system. Generally, it may be preferred to carry out the reaction at a sufficiently high temperature for the reaction mixture to be a one-phase system. Cooling of a one-phase reaction mixture from step (a) will lead to a separation of the aqueous and organic phases, for separation in step (b).

In step (b), the products obtained from step (a) are separated into an aqueous phase comprising a hemicellulose-derived monosaccharide and an organic phase comprising a $C_{3-8}$ alkyl ester. The hemicellulose-derived monosaccharides preferentially partition into the aqueous phase and the $C_{3-8}$ alkyl esters preferentially partition into the organic phase. Accordingly, use of the process of the invention results in the separation of organic acids from hemicellulose-derived monosaccharides, by conversion of the acids into their $C_{3-8}$ alkyl esters and carrying out liquid-liquid extraction. This separation results in an improved purity saccharide feedstock for possible onward reaction, for example reaction with metal hydroxide or quaternary ammonium hydroxide in step (c).

Where the hemicellulosic stream contains lignin and/or lignin-derived products, typically the lignin and/or lignin-derived products preferentially partition into the organic phase also. In one embodiment, preferably the reaction mixture obtained from step (a) comprises lignin and/or lignin-derived products, and step (b) comprises separating the reaction mixture into an aqueous phase comprising hemicellulose-derived monosaccharide and an organic phase comprising $C_{3-8}$ alkyl ester as well as lignin and/or lignin-derived products. Accordingly the process of the invention also provides for separation of lignin/lignin-derived products from hemicellulose-derived monosaccharides, again improving the purity of the feedstock that is reacted with metal hydroxide or quaternary ammonium hydroxide in step (c).

As discussed above, where a $C_{4-8}$ alkyl alcohol containing only one hydroxy group is used, a biphasic mixture results following step (a) without the need for additional organic solvent. However, if desired, additional organic solvent and/or water may be added prior to separation. For example, additional organic solvent may be used to wash the aqueous phase following initial separation from the organic phase in order to improve the purity of the saccharides present in the aqueous phase. Similarly, additional water may be used for re-extraction of the separated organic phase to increase the quantity of saccharides obtained. In one preferred embodiment, where additional organic solvent is used in step (b) the additional organic solvent is a $C_{4-8}$ alkyl alcohol containing only one hydroxy group, and the same type of alkyl alcohol is used in steps (a) and (b); more preferably the $C_{4-8}$ alkyl alcohol used in step (a) and additional organic solvent used in step (b) are both n-butanol.

In step (b) the organic and aqueous phases may be separated by routine techniques; for example by removing the bottom layer from a vessel through a bottom run-off valve, by decanting or siphoning off the top layer, or in a liquid-liquid phase separator. Step (b) may be carried out at ambient temperature, or at a higher or lower temperature if desired. In a preferred embodiment, step (b) is carried out at elevated temperature, preferably at a temperature in the range of from 30 to 95° C., more preferably in the range of from 40 to 90° C. Step (b) is typically carried out at ambient pressure, but it may be carried out at higher or lower pressure if desired.

In optional step (c), the hemicellulose-derived monosaccharide is reacted with a metal hydroxide or quaternary ammonium hydroxide to produce metal lactate or quaternary ammonium lactate. The non-fermentation conditions of step (c) are particularly suitable for use with the monosaccharide-containing aqueous phase produced in step (b).

In one embodiment the hemicellulose-derived monosaccharide is combined with another saccharide-containing feedstock prior to reaction with metal hydroxide or quaternary ammonium hydroxide. In another embodiment the hemicellulose-derived monosaccharide is not combined with another saccharide-containing feedstock prior to reaction with metal hydroxide or quaternary ammonium hydroxide.

In one preferred embodiment, a metal hydroxide is used in step (c), for example an alkali metal or alkaline earth metal hydroxide. Preferably the metal hydroxide is selected from the group consisting of lithium hydroxide, potassium hydroxide, sodium hydroxide, calcium hydroxide and barium hydroxide; more preferably the metal hydroxide is sodium hydroxide or barium hydroxide; most preferably the metal hydroxide is sodium hydroxide.

Examples of quaternary ammonium hydroxides include tetraalkylammonium hydroxides such as tetramethylammonium hydroxide and tetraethylammonium hydroxide, and benzylalkylammonium hydroxides such as benzyltrimethylammonium hydroxide.

Step (c) is typically carried out in the presence of one or more solvents. In particular, step (c) is normally carried out in the presence of water. The reaction between the hemicellulose-derived monosaccharide and metal hydroxide or quaternary ammonium hydroxide may also, if desired, take place in the presence of one or more organic solvents, for example an oxygenate such as an alcohol, ester, ether, or ketone solvent; and/or in the presence of one or more reactive extractants such as an amine. However, in a preferred embodiment, no organic solvent is admixed with the aqueous phase produced in step (b) prior to carrying out step (c). In one preferred embodiment water is the only solvent present in step (c).

Step (c) is preferably carried out at elevated temperature, for example at a temperature of up to 160° C. Preferably, hemicellulose-derived monosaccharide is reacted with metal hydroxide at a temperature in the range of from 50 to 140° C., more preferably in the range of from 60 to 120° C. In one embodiment step (c) is carried out at a temperature in the range of from 105 to 130° C. In one embodiment, hemicellulose-derived monosaccharide is reacted with metal hydroxide in water at reflux.

Step (c) is typically carried out at ambient pressure, but it may be carried out at higher or lower pressure if desired. Step (c) is typically carried out under ambient or inert atmosphere (e.g. under $N_2$ atmosphere).

In a preferred embodiment, step (c) is carried out batch-wise and hemicellulose-derived monosaccharide in water is added to an aqueous solution of metal hydroxide over a period of time at elevated temperature. For example, a mixture comprising hemicellulose-derived monosaccharide and water may be added over a period of time to a mixture of metal hydroxide and water that is at elevated temperature, for example at reflux. Preferably the mixture is added over a period in the range of from at least 5 minutes to 12 hours, at least 5 minutes to 3 hours, or at least 5 minutes to 1 hour. In one preferred embodiment hemicellulose-derived monosaccharide is reacted with metal hydroxide over a period in the range of from 15 minutes to 3 hours. In one preferred embodiment hemicellulose-derived monosaccharide is reacted with metal hydroxide over a period in the range of from 10 minutes to 1 hour.

The ratio of metal hydroxide or quaternary ammonium hydroxide to hemicellulose-derived monosaccharide should be sufficient to effect high conversion of hemicellulose-derived monosaccharide to lactate. For example the molar ratio of hydroxide ions in the metal hydroxide or quaternary ammonium hydroxide to hemicellulose-derived monosaccharide may be up to 10:1.

However, one advantage of the process of the invention is that comparatively low levels of organic acid byproducts such as formic acid and/or acetic acid are typically present in the material from step (b), that may be reacted with metal hydroxide in step (c). As a result, the need to use additional metal hydroxide to neutralise acidic species is reduced. Accordingly, in one preferred embodiment the molar ratio of hydroxide ion present in the metal hydroxide or quaternary ammonium hydroxide, to hemicellulose-derived monosaccharide is in the range of from 1.5:1 to 6:1, more preferably in the range of from 1.5:1 to 4:1, still more preferably in the range of from 1.7:1 to 2.5:1, yet more preferably 1.7:1 to 2.1:1. In one embodiment the molar ratio of hydroxide ion present in the metal hydroxide or quaternary ammonium hydroxide, to hemicellulose-derived monosaccharide is in the range of from 1.5:1 to 2.5:1. In one embodiment the molar ratio of hydroxide ion present in the metal hydroxide or quaternary ammonium hydroxide, to hemicellulose-derived monosaccharide is in the range of from 1.5:1 to 2.1:1.

In one preferred embodiment of step (c), hemicellulose-derived monosaccharide is reacted with sodium hydroxide at a temperature in the range of from 50 to 140° C.

In one preferred embodiment, the aqueous hemicellulosic stream used in step (a) is a pre-hydrolysate liquor obtained from a process for producing dissolving pulp, and in step (a) the hemicellulosic stream is admixed with an acid selected from the group consisting of hydrochloric acid and sulfuric acid, and with n-butanol, at a temperature in the range of from 95 to 150° C.; and step (c) comprises reacting at least a portion of the hemicellulose-derived monosaccharide with sodium hydroxide, at a temperature in the range of from 50 to 140° C.

In one preferred embodiment, the aqueous hemicellulosic stream used in step (a) is a pre-hydrolysate liquor obtained from a process for producing dissolving pulp, and in step (a) the hemicellulosic stream is admixed with an acid selected from the group consisting of hydrochloric acid and sulfuric acid, and with n-butanol, at a temperature in the range of from 95 to 150° C., at ambient pressure, and over a time period in the range of from 2 to 6 hours; step (b) is carried out at elevated temperature; and step (c) comprises reacting at least a portion of the hemicellulose-derived monosaccharide with sodium hydroxide, at a temperature in the range of from 50 to 140° C., at ambient pressure, and over a time period in the range of from 15 minutes to 3 hours.

The metal lactate or quaternary ammonium lactate produced by the process of the invention when step (c) is included may for example be converted into lactic acid. Accordingly the invention provides a process comprising producing a metal lactate or a quaternary ammonium lactate by a process according to the invention; and (d) reacting at least a portion of the metal lactate or quaternary ammonium lactate with an acid to produce lactic acid. Typically step (d) is carried out at ambient temperature, although higher or lower temperatures may be used if desired. Step (d) is typically carried out under ambient or inert atmosphere (e.g. under $N_2$ atmosphere). The acid used in step (d) is preferably a mineral acid, more preferably hydrochloric acid or sulfuric acid. In one embodiment the same type of acid is used in step (d) as the acid used in step (a). Preferably the amount of acid used in step (d) should be sufficient to neutralise all or substantially all of the metal lactate or quaternary ammonium lactate present in the reaction mixture. As discussed above, an advantage of the process of the invention is that the quantities of metal hydroxide or quaternary ammonium lactate required in step (c) to effect good conversion of hemicellulose-derived monosaccharide to lactate are relatively low. As a result, the quantities of acid required to neutralise the metal lactate or quaternary ammonium lactate are also relatively low, resulting in reduced levels of salts requiring disposal and/or reprocessing. In one preferred embodiment the molar ratio of available protons present in the acid used in step (d), to hydroxide ions present in the metal hydroxide or quaternary ammonium hydroxide used in step (c), is in the range of from 0.9:1 to 2:1, more preferably in the range of from 0.9:1 to 1.5:1; still more preferably in the range of from 0.9:1 to 1.1:1.

The lactic acid produced in step (d) may also be converted into other downstream products such as, for example, an alkyl lactate. Thus the invention also provides a process for producing an alkyl lactate comprising producing lactic acid by a process according to the invention; and (e) reacting the lactic acid with an alkyl alcohol. Preferably the alkyl alcohol used in step (e) is a $C_{1-6}$ alkyl alcohol, more preferably a $C_{1-6}$ alkyl alcohol containing only one hydroxy group (e.g. ethanol, n-propanol, i-propanol, n-butanol, n-pentanol, n-hexanol), more preferably a $C_{3-6}$ alkyl alcohol containing only one hydroxyl group, most preferably the alkyl alcohol is n-butanol. In one embodiment the same type of alkyl alcohol is used in steps (a) and (e); preferably the alkyl alcohol used in steps (a) and (e) is n-butanol. Step (e) may be carried out in the presence of a catalyst, for example an acid catalyst (e.g. a mineral acid, such as hydrochloric acid or sulfuric acid, or an organic acid such as lactic acid, or a solid acid, such as a resin-supported acid or an acidic zeolite). In such cases it is normally preferred to use an excess of acid in step (d) compared with the metal hydroxide or quaternary ammonium hydroxide used in step (c), e.g. the molar ratio of available protons present in the acid used in step (d), to hydroxide ions present in the metal hydroxide or quaternary ammonium hydroxide used in step (c), may be in the range of from 1.01:1.00 to 1.50:1, preferably in the range of from 1.01:1.00 to 1.20:1.00; more preferably in the range of from 1.01:1.00 to 1.10:1.00. Step (e) is suitably carried out at elevated temperature, for example at a temperature in the range of from 50 to 150° C. Where the product mixture from step (d) contains water, water may be removed from the mixture during step (e), for example by evaporation or distillation. Water produced by the reaction of lactic acid with alcohol is also typically removed as it is formed. For example a mixture containing water, $C_{1-6}$ alkyl alcohol (e.g. n-butanol), lactic acid and mineral acid (e.g. HCl or $H_2SO_4$) may be heated under reflux with water being removed (e.g. as an azeotropic mixture).

Additional reagents or processing steps may also be used at any stage of the process.

Typically racemic metal lactate, quaternary ammonium lactate, lactic acid or alkyl lactate is produced by the processes described above, each of which can be converted into further downstream products by routine methods. Unless a resolution step is carried out, the downstream products will typically be racemic also. The invention also provides a process for producing lactic acid, alkyl lactate, oligomeric lactic acid, lactide, alkyl lactyllactate, polylactic acid, or a complex of lactic acid and either ammonia or an amine, comprising producing metal lactate or quaternary ammonium lactate by a process according to the invention, and converting the metal lactate or quaternary ammonium lactate into lactic acid, alkyl lactate, oligomeric lactic acid, lactide, alkyl lactyllactate, polylactic acid, or said complex. The invention also provides a process for producing alkyl lactate, oligomeric lactic acid, lactide, alkyl lactyllactate, polylactic acid, or a complex of lactic acid and either ammonia or an amine, comprising producing lactic acid by a process according to the invention, and converting the lactic acid into alkyl lactate, oligomeric lactic acid, lactide, alkyl lactyllactate, polylactic acid, or said complex. The invention also provides a process for producing lactic acid, oligomeric lactic acid, lactide, alkyl lactyllactate, polylactic acid, or a complex of lactic acid and either ammonia or an amine, comprising producing a alkyl lactate by a process according to the invention, and converting the alkyl lactate into lactic acid, oligomeric lactic acid, lactide, alkyl lactyllactate, polylactic acid, or said complex.

For example, metal lactate or quaternary ammonium lactate may be converted into a complex of lactic acid and either ammonia or an amine by converting the metal lactate or quaternary ammonium lactate into lactic acid as described above, and reacting the lactic acid with an amine or ammonia to produce the complex. Where barium hydroxide is used and barium lactate is produced, it may also be converted into a complex of lactic acid and either ammonia or an amine, as described in, for example, WO2012/052703.

Metal lactate or quaternary ammonium lactate may also be converted into alkyl lactate, for example via conversion into lactic acid and then heating with alkyl alcohol as described above. Alternatively metal lactate may be converted into complex, and the complex may then be converted into alkyl lactate, for example by heating the complex to remove ammonia or amine, and heating in the presence of an alkyl alcohol (e.g. methanol, ethanol, n-propanol, isopropanol, n-butanol) to produce the alkyl lactate. In a further example, a quaternary alkylammonium lactate may be heated to produce alkyl lactate and the corresponding trialkylamine. As discussed above, the metal lactate or quaternary ammonium lactate produced by the process of the invention will typically be racemic (i.e. it contains substantially equal proportions of (S)-lactate and (R)-lactate anions). As a result, except in the case where a resolution step is carried out to separate enantiomers, a mixture of alkyl lactates will normally be obtained (e.g. a mixture of alkyl (R)-lactate and alkyl (S)-lactate).

Metal lactate or quaternary ammonium lactate may also be converted into oligomeric lactic acid, for example by conversion into lactic acid, complex or alkyl lactate as described above, and by heating the lactic acid, complex or alkyl lactate, and removing water, amine or ammonia and/or alcohol.

Metal lactate or quaternary ammonium lactate may also be converted into lactide, a cyclic dimer of lactic acid that is itself useful in the production of polylactic acid. For example, metal lactate or quaternary ammonium lactate may be converted into oligomeric lactic acid as described above, and the oligomeric lactic acid may be converted into lactide by heating in the presence of a transesterification catalyst. There are three forms of lactide, (S,S)- or L-lactide, (R,R)- or D-lactide, and (R,S)- or meso-lactide. As discussed above, the metal lactate or quaternary ammonium lactate produced by the process of the invention will typically be racemic (i.e. it contains substantially equal proportions of (S)-lactate and (R)-lactate anions). As a result, except in the case where a resolution step is carried out, a mixture of lactides will normally be obtained. (R,S)-lactide may be separated from (S,S)-lactide and (R,R)-lactide by standard separation techniques, for example by distillation, solvent extraction, or crystallisation.

Metal lactate or quaternary ammonium lactate may be converted into alkyl lactyllactate, for example by conversion into lactide, and reacting the lactide with an alkyl alcohol to produce alkyl lactyllactate. Where (R,R)-lactide is reacted, the alkyl lactyllactate will be largely alkyl (R,R)-lactyllactate. Where (S,S)-lactide is reacted, the alkyl lactyllactate will be largely alkyl (S,S)-lactyllactate.

Metal lactate or quaternary ammonium lactate may also be converted into polylactic acid, for example by conversion into lactide, and polymerising the lactide to produce polylactic acid (e.g. by contacting with a catalyst at elevated temperature). Where (R,R)-lactide ID polymerised, poly (R)-lactic acid is produced. Where (S,S)-lactide is polymerised, poly (S)-lactic acid is produced. Poly (R)-lactic acid may be combined with poly (S)-lactic acid, for example using melt blending, to produce stereocomplex polylactic acid.

Additional routine processing steps may be carried out at any stage of the process, e.g. to add or remove solvent. By way of example, the aqueous hemicellulosic stream may be concentrated to remove some water prior to carrying out step (a), and/or the aqueous phase obtained in step (b) may be concentrated to remove some water prior to carrying out step (c) (e.g. by distillation, evaporation or membrane separation).

The following Examples illustrate the invention.

Figure 2:
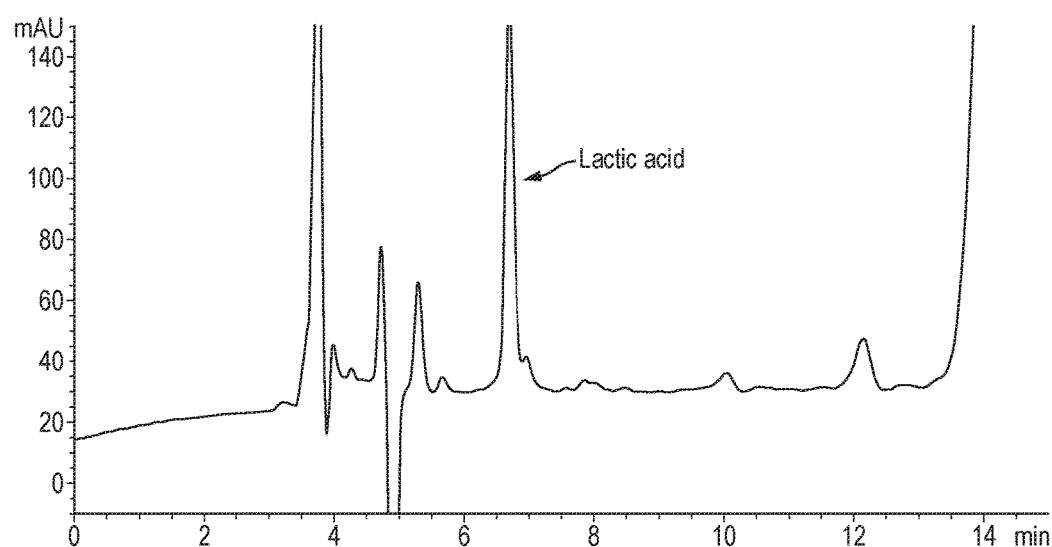
FIG. 2 shows an HPLC chromatogram of an aqueous reaction mixture following treatment of xylan with aqueous sulfuric acid and n-butanol at reflux for 3 hours, separation of the aqueous and organic layers, and treatment of the aqueous layer with aqueous sodium hydroxide over 60 minutes at elevated temperature, and subsequent acidification. The HPLC chromatogram shows the presence of lactic acid.

Example 1: Production of Sodium Lactate and Lactic Acid from Hemicellulosic Stream a) To a 250 mL flask was charged xylan (3.301 g, from beech wood, Sigma-Aldrich, 96.4% purity based on HPLC area) followed by water (50 mL), concentrated $H_2SO_4$ (0.5 mL) and n-butanol (30 mL, purity determined by GC analysis, see FIG. 3). The suspension was stirred and heated to reflux for 3 hours during which all the suspended tarry material dissolved.

b) The reaction mixture was then cooled to ambient temperature and the layers were separated. The organic n-butanol layer was dark coloured, consistent with the removal of lignin residues, and the lower aqueous layer was pale straw/yellow coloured. Analysis of the n-butanol layer by GC indicated the presence of butyl acetate (FIG. 4). Analysis of the aqueous layer by HPLC showed no visible peak corresponding to acetic acid (FIG. 1).

c) The separated aqueous layer (50.9 g) was then added over a period of 60 min to 50% aqueous sodium hydroxide solution (8.2 mL) at 100-120° C. The reaction mixture was then cooled to ambient temperature and acidified with 10 mL concentrated (37%) HCl to achieve a pH <3 and made up to 1 L with water in a volumetric flask and analysed by HPLC, indicating a lactic acid yield of 0.84 g (FIG. 2).

Example 2: Processing of a Pre-Hydrolysate Liquor as Hemicellulosic Stream (i) Analysis of Hemicellulosic Stream (Pre-Hydrolysate Liquor) for Acids Samples of pre-hydrolysate liquor obtained from a commercial dissolving pulp process were analysed for acetic acid and formic acid content (by HPLC) as well as lignin content (by UV spectroscopy) and found to contain the following concentrations: acetic acid, 0.64% w/v; formic acid, 0.07% w/v; and lignin, 0.65% w/v.

(ii) Determination of Saccharide Content

To a measured amount of pre-hydrolysate liquor, sulphuric acid (1% v/v based on the volume of PHL) was added and the suspension was heated to reflux for three hours. The reaction mixture was cooled and analysed for monosaccharide content by IC specific for monosaccharides. The results indicated that the hydrolysis generated mainly xylose (2.48% w/v) with some glucose, arabinose, galactose and mannose.

(iii) Concentration of Pre-Hydrolysate Liquor:

To a 2000 mL evaporating flask was charged 1000 mL of pre-hydrolysate liquor. The suspension was stirred and heated to 55° C. on a rotary evaporator and 760 mL distillate was removed under reduced pressure (140-95 mbar), leaving 240 mL of concentrated pre-hydrolysate liquor which was used as a stock solution in the following experiments. The distillate was analysed for acetic and formic acid content by HPLC and was found to contain 3.02 mg/mL of acetic acid and 0.02 mg/mL of formic acid. This equates to 22.4% w/w removal of total acetic acid and 21.7% w/w removal of total formic acid. The concentration of the monosaccharides and lignin were assumed to have increased pro-rata.

Example 2(a): Treatment of Concentrated Pre-Hydrolysate Liquor Using Aqueous HCl To a 250 mL round bottomed flask equipped with reflux condenser was charged the concentrated pre-hydrolysate liquor (50 mL/54.0 g) followed by concentrated hydrochloric acid (2.5 mL) and n-butanol (30 mL). The biphasic mixture was stirred and heated to reflux for three hours during which all the colour and suspended solids dissolved. The reaction mixture was then cooled to ambient temperature and the layers were separated. The organic phase was dark coloured and the lower aqueous phase was pale straw/yellow coloured.

The separated aqueous phase (49 mL) was analysed for monosaccharide and lignin content and the following results were found:

| xylose % w/v | glucose % w/v | arabinose % w/v | galactose % w/v | mannose % w/v | lignin % w/v | lignin extracted % w/w |
|---|---|---|---|---|---|---|
| 8.34 | 0.42 | 0.23 | 0.38 | 0.82 | 0.24 | 91.5 |

The separated organic phase (35 mL) was analysed for butyl acetate and butyl formate (by GC) and was found to contain 35.42 mg/mL butyl acetate and 3.62 mg/mL butyl formate. This equates to 30.0% w/w removal of total acetic acid and 38.8% w/w removal of total formic acid.

Example 2(b): Treatment of Concentrated Pre-Hydrolysate Liquor Using Aqueous HCl To a 250 mL round bottomed flask equipped with reflux condenser was charged concentrated pre-hydrolysate liquor (50 mL/54.4 g) followed by concentrated hydrochloric acid (2.5 mL). The suspension was stirred and heated to reflux for three hours and cooled to ambient temperature. To this reaction mixture, n-butanol (30 mL) was added and the biphasic mixture was stirred and heated to reflux for 1 hour during which all the colour and suspended solids dissolved. The reaction mixture was then cooled to ambient temperature and the layers were separated. The organic phase was dark coloured and the lower aqueous phase was pale straw/yellow coloured. The separated aqueous phase (49 mL) was analysed for monosaccharide and lignin content and the following results were found:

| xylose % w/v | glucose % w/v | arabinose % w/v | galactose % w/v | mannose % w/v | lignin % w/v | lignin extracted % w/w |
|---|---|---|---|---|---|---|
| 8.60 | 0.49 | 0.14 | 0.37 | 0.95 | 0.22 | 92.1 |

The separated organic phase (30 mL) was analysed for butyl acetate and butyl formate (by GC) and was found to contain 38.66 mg/mL butyl acetate and 4.17 mg/mL butyl formate. This equates to 28.1% w/w removal of total acetic acid and 38.3% w/w removal of total formic acid.

Example 2(c): Treatment of Concentrated Pre-Hydrolysate Liquor Using $H_2SO_4$

To a 250 mL round bottomed flask equipped with reflux condenser was charged the concentrated pre-hydrolysate liquor (50 mL/54.3 g) followed by concentrated sulphuric acid (1.6 mL) and n-butanol (30 mL). The biphasic mixture was stirred and heated to reflux for three hours during which all the colour and suspended solids dissolved. The reaction mixture was then cooled to ambient temperature and the layers were separated. The organic phase was dark coloured and the lower aqueous phase was pale straw/yellow coloured.

The separated aqueous phase (47.5 mL) was analysed for monosaccharide and lignin content and the following results were found:

| xylose % w/v | glucose % w/v | arabinose % w/v | galactose % w/v | mannose % w/v | lignin % w/v | lignin extracted % w/w |
|---|---|---|---|---|---|---|
| 8.86 | 0.43 | 0.22 | 0.40 | 0.91 | 0.25 | 91.2 |

The separated organic phase (34.5 mL) was analysed for butyl acetate and butyl formate (by GC) and was found to contain 37.07 mg/mL butyl acetate and 4.15 mg/mL butyl formate. This equates to 30.9% w/w removal of total acetic acid and 43.9% w/w removal of total formic acid.

Example 2(d): Treatment of Concentrated Pre-Hydrolysate Liquor Using Aqueous $H_2SO_4$ To a 250 mL round bottomed flask equipped with reflux condenser was charged the concentrated hydrolysate liquor (50 mL/54 g) followed by concentrated sulphuric acid (1.6 mL). The suspension was stirred and heated to reflux for three hours and cooled to ambient temperature. To this reaction mixture, n-butanol (30 mL) was added and the biphasic mixture was stirred and heated to reflux for one hour during which all the colour and suspended solids dissolved. The reaction mixture was then cooled to ambient temperature and the layers were separated. The organic phase was dark coloured and the lower aqueous phase was pale straw/yellow coloured. The separated aqueous phase (47 mL) was analysed for monosaccharide and lignin content and the following results were found:

| xylose % w/v | glucose % w/v | arabinose % w/v | galactose % w/v | mannose % w/v | lignin % w/v | lignin extracted % w/w |
|---|---|---|---|---|---|---|
| 9.11 | 0.49 | 0.22 | 0.42 | 1.01 | 0.27 | 90.5 |

The separated organic phase (35 mL) was analysed for butyl acetate and butyl formate (by GC) and was found to contain 38.02 mg/mL butyl acetate and 4.76 mg/mL butyl formate. This equates to 32.2% w/w removal of total acetic acid and 51.1% w/w removal of total formic acid.

The invention claimed is:
1. A method of processing an aqueous hemicellulosic stream, comprising:
  (a) contacting an aqueous hemicellulosic stream with a $C_{3-8}$ alkyl alcohol at elevated temperature and acidic pH to produce a reaction mixture comprising a $C_{3-8}$ alkyl ester and a hemicellulose-derived monosaccharide; and

(b) separating the reaction mixture obtained from step (a) into an aqueous phase comprising said hemicellulose-derived monosaccharide and an organic phase comprising said $C_{3-8}$ alkyl ester;

wherein the aqueous hemicellulosic stream comprises saccharide materials derived from lignocellulosic biomass; and at least 60 wt. % of the saccharide materials derived from the lignocellulosic biomass in the hemicellulosic stream are hemicellulosic materials.

2. The process as claimed in claim 1, wherein step (a) is carried out at a temperature of from 70° C. to 200° C.

3. The process as claimed in claim 1, wherein step (a) is carried out at a temperature of from 95° C. to 150° C.

4. The process as claimed in claim 1, wherein the hemicellulosic stream comprises lignin.

5. The process as claimed in claim 4, wherein the reaction mixture obtained in step (a) comprises lignin and/or lignin-derived products, and wherein the organic phase separated in step (b) comprises said lignin and/or lignin-derived products.

6. The process as claimed in claim 1, wherein in step (a) the aqueous hemicellulosic stream is admixed with an acid.

7. The process as claimed in claim 6, wherein the acid is selected from the group consisting of hydrochloric acid and sulfuric acid.

8. The process as claimed in claim 1, wherein the aqueous hemicellulosic stream has been obtained by the treatment of biomass using a process which does not comprise treating the biomass with an alcohol.

9. The process as claimed in claim 8, wherein the aqueous hemicellulosic stream has been obtained by the treatment of biomass using one of the following methods: treatment with alkaline agents; treatment with liquid ammonia; treatment with compressed liquid hot water or steam; or a process for producing dissolving pulp.

10. The process as claimed in claim 9, wherein the aqueous hemicellulosic stream is a pre-hydrolysate liquor obtained from a process for producing dissolving pulp.

11. The process as claimed in claim 10, in which the process for producing dissolving pulp involves the hydrolysis of wood chips using hot water under pressure, or using steam.

12. The process as claimed in claim 1, wherein the $C_{3-8}$ alkyl alcohol is a $C_{3-6}$ alkyl alcohol.

13. The process as claimed in claim 12, wherein the $C_{3-8}$ alkyl alcohol is n-butanol.

14. The process as claimed in claim 1, which comprises the additional step:

(c) reacting said hemicellulose-derived monosaccharide obtained from step (b) with a metal hydroxide or a quaternary ammonium hydroxide to produce a metal lactate or quaternary ammonium lactate.

15. The process as claimed in claim 14, wherein in step (c) said hemicellulose-derived monosaccharide is reacted with a metal hydroxide.

16. The process as claimed in claim 15, wherein the metal hydroxide is sodium hydroxide.

17. The process as claimed in claim 14, wherein the molar ratio of hydroxide ions present in the metal hydroxide or quaternary ammonium hydroxide used in step (c), to hemicellulose-derived monosaccharide, is in the range of from 1.5:1 to 4:1.

18. The process as claimed in claim 14, wherein step (c) is carried out at a temperature in the range of from 50 to 140° C.

19. The process as claimed in claim 14, which comprises the additional step:

(d) reacting at least a portion of the metal lactate or quaternary ammonium lactate with an acid to produce the lactic acid.

20. The process as claimed in claim 19, which comprises the additional step:

(e) reacting at least a portion of the lactic acid with an alkyl alcohol to produce an alkyl lactate.

21. The process as claimed in claim 14, which comprises the additional step of:

converting the metal lactate or quaternary ammonium lactate produced in step (c) into lactic acid, alkyl lactate, oligomeric lactic acid, lactide, alkyl lactyllactate, polylactic acid, or said complex.

* * * * *